United States Patent [19]

Morcos et al.

[11] Patent Number: 5,497,770
[45] Date of Patent: Mar. 12, 1996

[54] TISSUE VIABILITY MONITOR

[75] Inventors: N. Charle Morcos, Irvine; Roger A. Nahas, Marina del Rey, both of Calif.

[73] Assignee: The Regents of the University of California, Oakland, Calif.

[21] Appl. No.: 182,264

[22] Filed: Jan. 14, 1994

[51] Int. Cl.⁶ ............................................ A61B 5/00
[52] U.S. Cl. ................. 128/633; 128/664; 128/665; 128/666
[58] Field of Search ........................... 128/632–635, 128/664–666

[56] References Cited

U.S. PATENT DOCUMENTS

| | | | |
|---|---|---|---|
| 4,223,680 | 9/1980 | Joebsis | 128/633 |
| 4,281,645 | 8/1981 | Joebsis | 128/633 |
| 4,513,751 | 4/1985 | Abe et al. | 128/666 |
| 4,693,255 | 9/1987 | Beall | 128/665 |
| 4,877,034 | 10/1989 | Atkins et al. | 128/664 |
| 5,054,916 | 10/1991 | Kanda et al. | 128/666 |
| 5,074,306 | 12/1991 | Green et al. | 128/664 |
| 5,127,408 | 7/1992 | Parsons et al. | 128/634 |
| 5,161,531 | 11/1992 | Parsons et al. | 128/634 |
| 5,227,308 | 7/1993 | Jameson et al. | 128/665 |

OTHER PUBLICATIONS

R. J. Barnard, et al., "Studies of Controlled Reperfusion After Ischemia—III. Histochemical studies: Inability of triphenyltetrazolium chloride nonstaining to define tissue necrosis," *J. Thorac. Cardiovasc. Surg.*, 92:502–12 (1986).

M. R. Milunski, et al., "Ultrasonic Tissue Characterization With Integrated Backscatter," *Circulation*, 80:491–503 (1989).

N. C. Morcos et al., "$(CA^{2+}+Mg^{2+})$–ATPase in enriched sarcolemma from dog heart," *Biochim. Biophys. Acta*, 598:27–39 (1980).

N. C. Morcos, "Localization of $(CA^{2+}+Mg^{2+})$–ATPase, $CA^{2+}$ pump and other ATPase activities in cardiac sarcolemma," *Biochim. Biophys. Acta*, 688:747–56 (1982).

W. J. Parsons et al., "Dynamic Mechanisms of Cardiac oxygenation during brief ischemia and reperfusion," *J. Physiol. Heart Circ. Physiol.*, vol. 259(5):H1477–85 (1990).

*Primary Examiner*—Ruth S. Smith
*Attorney, Agent, or Firm*—Crosby, Heafey, Roach & May

[57] ABSTRACT

A method and apparatus for evaluating the viability of a tissue of interest, particularly that presents as dead but may be merely stunned or hibernating with reduced or no contractility. Dynamic measurement of oxidative metabolism permits distinguishing between different stages of compromised myocardium. Measurements can be made using near-infrared illumination and detection coupled with infusion of one or more metabolic substrates to the region of interest to evaluate whether a metabolic pathway cascade or a transmembrane ionic potential are intact and thereby provide an indication of the viability of the cell.

20 Claims, 3 Drawing Sheets

TISSUE VIABILITY MONITOR

FIELD OF THE INVENTION

The present invention relates to a method and apparatus for measuring metabolic activity in body organs or tissues for the purpose of determining their viability. More particularly, the present invention relates to a method and apparatus for measuring metabolic activity in body organs or tissues that are viable, but appear to be stunned or possibly dead. More particularly, the invention relates to a method and apparatus for spectrophotometric examination of an endocardial or epicardial region of interest and also providing for infusion of one or more metabolic substrates to the region of interest to evaluate whether a metabolic pathway cascade or a transmembrane ionic potential are intact and provide an indication of the viability of the cell.

BACKGROUND

The last decade of cardiac surgery has witnessed significant strides towards better understanding and better management of previously lethal cardiac pathology.

Two important manifestations stand out in particular. First, the decade has witnessed a remarkable improvement in techniques for preserving the myocardium (heart muscle) from irreversible damage, coupled with a widening choice of sophisticated ways to correct myocardial ischemia. Second, practitioners generally recognize new conditions such as myocardial stunning and hibernation where the injured myocardium is in a state of "suspended animation," closely resembling total necrosis but very different in practice since it retains enough viability to allow for function retrieval by modem techniques. Varying intermediate degrees of the above situations have also been identified.

Faced with the recognition of this widening variety of ischemic clinical pictures with variable degrees of retained viability, and armed with the knowledge that several conditions previously considered hopeless can now be salvaged if appropriately recognized as viable, cardiologists and cardiac surgeons are increasingly aware of the need to optimize selection from their ever-widening choice of techniques in a way that matches the particular clinical situation.

By necessity, such a goal would depend on our ability to assess viability in an injured myocardium as accurately as possible.

The regional nature of coronary occlusive disease produces a need for a non-invasive means of assessing regional oxidative metabolism in cardiac patients. To those familiar with this art, there is no method presently known of accurately and quickly measuring regional tissue oxygen availability and utilization in human beings. Standard clinical indicators are insensitive to the non-uniform drop-out of myocardial perfusion-metabolism units associated with coronary insufficiency. Radionuclide and angiographic methods permit the evaluation of myocardial perfusion and ventricular wall motion, but the metabolic state of the myocardium cannot be reliably predicted with these methods, particularly in patients with marginal perfusion and/or abnormal ventricular wall motion.

Current methods for assessing myocardial viability each have significant shortcomings. (1) The "educated clinical guess" is based on EKG readings and cardiac enzyme measurements, angiographic evidence of ventricular contractility and collateral circulation. This provides a sound general assessment but lacks the accuracy needed to fine-tune the clinical and surgical management. (2) Thallium 201 perfusion/redistribution studies are used to outline regions of cardiac ischemia or scarring. Unfortunately, these studies are time consuming, cannot be applied to acute conditions, and have been proved inaccurate in diagnosing sear in 32% of cases (as shown by PET scanning). (3) Position emission tomography (PET) scanning utilizes a radioactive metabolic tracer, usually a glucose analogue, to follow tracer uptake by viable myocardial cells, as detected by positron emission. This method is the most accurate detector of viable myocardium so far but it is complicated and quite expensive, and is not practical in the acute phase so it is only used in a few academic centers. (4) Biopsy specimens may show metabolic and structural signs of irreversible damage such as the adenosine triphosphate (ATP) intracellular levels and triphenyltetrazolium chloride (TTC) vital staining (or lack thereof). Although these tests were previously accepted as reliable, they have now been found to be inaccurate. R. J. Barnard, et al., "Studes of Controlled Reperfusion After Ischemia - III. Histochemical studies: Inability of triphenyltetrazolium chloride non-staining to define tissue necrosis," *J. Thorac. Cardiovasc. Surg.* 92:502-12 (1986). For example, a recently neefolio cell or stunned myocardium will show similar low levels of ATP yet the stunned myocardium could be saved if recognized and treated promptly. Of the presently available methods, PET scanning comes closest to fulfilling the need for assessing viability. However, it is expensive, often impractical and still does not help in the acute phase.

Some methods of measuring myocardial metabolism such as Magnetic Resonance Imaging/Spectroscopy and Positron Emission Tomography are costly and require cumbersome equipment (magnets and cyclotrons) which are not compatible with the cardiac catheterization laboratory setting found in most hospitals and/or clinics. The test procedures also require considerable time to carry out, and a patient suffering an acute heart attack generally cannot be evaluated by these methods with enough time left to implement a corrective procedure.

The capacity to rapidly discern the metabolic state of the beating human heart, particularly within abnormally contracting myocardial segments, would beneficially affect clinical decisions regarding the need for therapeutic interventions such as blood clot dissolving agents, balloon angioplasty, and coronary artery bypass grafting.

Several researchers have worked on steady state evaluations using a variety of spectrophotometric methods. A good review of the prior art spectrophotometric methods for measuring circulatory and respiratory functions, arterial blood oxygenation and blood samples is set forth in U.S. Pat. Nos. 4,223,680 and 4,281,645 to Jöbsis. The application of differential spectroscopy using near infrared (NIR) light in blood perfused body organs was advanced by Jöbsis as described in detail in the aforementioned patents.

Jöbsis emphasized in these patents that near infrared (NIR) light must span a relatively long path (e.g. several centimeters) in length in order for his invention to work. The long pathlength is significant in that it allows the light photons to travel deeply into the tissue of interest so that the received optical signal will contain information from a substantial volume of tissue. Also, the longer path length minimizes the light-scattering effects of structures which are superficial to the region of interest. Since, as shown in FIG. 2 of U.S. Pat. No. 4,223,680, the back-scattered light from superficial structures may not contain metabolic information of interest, and may obscure detection of the desired metabolic information, a method was sought by Jöbsis to minimize this biophysical effect. Accordingly, both Jöbsis patents teach that the near infrared (NIR) light must be transmitted to the test organ (in situ) and then the radiation intensity must be detected and measured at a point spaced apart from the point of light entry. As indicated in FIG. 1 and FIG. 2 of U.S. Pat. No. 4,223,680, the physical distance between entrance and exit of near infrared (NIR) light is specified to be several centimeters.

Others follow the Jöbsis teaching that the light detector fiber bundle must be spaced apart from the light source fiber bundle to minimize light scattering from superficial tissue regions. Parsons et al., in U.S. Pat. Nos. 5,161,531 and 5,127,409 disclose bundles spaced apart even if the light source fiber bundle and light detector fiber bundle are oriented parallel to each other as suggested by Abe in U.S. Pat. No. 4,513,751. Simply transmitting near infrared (NIR) light down one optical fiber and receiving the reflected light with a second optical fiber which is parallel and immediately adjacent to the transmitting fiber, as proposed by Abe for visible light wavelengths, will not permit the desired accurate near infrared (NIR) measurement of oxidative metabolism within a substantial tissue volume.

Summarily, it is highly desirable for intravascular application of a red to near-infrared (NIR) light sending and receiving device that a single scope containing both the transmitting and receiving optical fibers be used to acquire optical information from an endocardial site. The introduction of two separate send and receive scopes by a percutaneous, intravascular approach to the endocardium would be hampered by motion artifact of the beating myocardial wall and the instability of the optical alignment of the two scopes relative to the tissue region of interest. Parsons et al. sought to overcome the shortcomings of the prior art as disclosed in the Jöbsis and Abe patents by using a steerable fiber optic device to deliver and receive near infrared (NIR) light through a single small-diameter scope (less than 3.3 mm in diameter) positioned at the endocardial surface by means of a percutaneous intravascular approach which is applicable in a standard clinical catheterization laboratory. The procedure using the Parsons et al. device can be done as part of a routine diagnostic catheterization study, and permits the steady-state measurement of regional myocardial oxygenation from within the beating heart.

A variety of products and devices that enter the myocardium are currently used to evaluate tissue status.

| Products | Primary Users |
|---|---|
| Cardiac catheters | Cardiologists |
| Electrophysiology pacing wires | Cardiologists, Surgeons |
| Biopsy device | Surgeons |
| Hemo-pump | Surgeons |
| Intravascular ultrasound | Cardiologists |
| Atherectomy device/catheter | Cardiologists |
| Laser fibers | Cardiologists |
| Coronary angioscope | Cardiologists |

Many of these procedures are performed on a daily basis in most acute care centers with cardiac catheterization being the most frequent intervention. No valvular damage is caused by any of these devices as they cross the valves. Stenotic (narrowed) valves in certain diseases may not allow passage of the catheter. Prosthetic valves do not allow passage of the catheter.

Prospect For PET, NMR, and Ultrasound Backscatter Technology

Positron emission tomography (PET) has many limitations, many of which are anticipated to be insurmountable over the next 3–5 years. PET is a large expensive device. It is therefore rarely available even in large medical centers. Miniaturization of the technology and reduction of its cost is most unlikely over the next five years. A good example of this is Nuclear Magnetic Resonance (NMR) technology, also known as magnetic resonance imaging (MRI). NMR is a very old technology, originally developed over 40 years ago. To date, MRI imaging machines are very large, very expensive and only sometime available even in large medical centers. Similarly, computerized axial tomography machines (CT or CAT scanners), although more widely available now, are still very large, expensive and require specific building and structural arrangement. Many hospitals rely on leasing mobile scanners or simply refer studies to outside service providers. Each of these difficulties means the analytical equipment is relatively less available but only limited time is available for evaluating viable tissue after an ischemic attack. This time is optimally one to two hours, although useful recovery is possible in some cases after several hours.

In addition to these limitations, PET scanners cannot detect myocardial damage in the acute state of myocardial infarction. Furthermore, it is very unlikely to place a patient suffering an acute myocardial infarction inside a large scanner in the radiology department for a prolonged period of time while images are being collected. More appropriately, such a patient should be in the cardiac catheterization laboratory where the heart can be eatheterized, myocardial wall viability assessed with the tissue viability monitor, and appropriate interventions performed.

A further serious limitation of the PET scanner is the need for a facility to generate radioactive isotope. Such facilities are large, expensive, and not usually present in many large cities. The isotope half-life is very short. The remoteness of the isotope generating facility from most cities and medical centers and the short half-life of the isotope require the special ordering of the isotope acutely for each selected case and the use of airlines to deliver the short-lived isotope, a sequence that is expensive, cumbersome and rarely available to most medical centers. Such limitations will not change significantly over the next five years and beyond.

Backscatter Ultrasound Technology

Transthoracic ultrasound technology has been used to evaluate cardiac tissue conditions, including some attempts to identify hibernating versus dead myocardium. M.R. Milunski, et al., "Ultrasonic Tissue Characterization With Integrated Backscatter," *Circulation*, 80:491–503 (1989). This technology is limited by the quality of the image. The ultrasound image is compromised by many factors including chest wall size, obesity and most importantly lung disease. A great majority of older patients have lung disease (e.g. chronic obstructive pulmonary disease or COPD) which significantly compromises the backscatter image quality. Many times these are the same patients who have cardiac problems as well and need evaluation. The present invention can be used in backscatter ultrasound evaluation to provide additional information about the physiological integrity of apparently dead tissue.

Without a clear transthoracic ultrasound image, current backscatter technology is somewhat limited. However, for some patients, backscatter may provide an alternative means for evaluating tissue viability. To overcome transthoracic poor image quality in many patients, echocardiography can be performed invasively by the transesophogeal approach.

Clinical Indications

There are many cardiac conditions which are life threatening and treatable, but the treatment itself is a major procedure which itself has an attendant risk to life. Cardiologists and cardiac surgeons would both benefit from a procedure which would identify cardiac tissue which has a good probability of returning to normal function. A useful assay would allow physicians to identify candidate tissue and also to select an appropriate mode of treatment.

Selected Clinical Situations that Present a Clinical Decision Dilemma and Benefit From Objective Evaluation of Viability A. Idiopathic dilated cardiomyopathy (IDCM)

In this disease the chamber wall is hypokinetic and chamber size dilated, resembling in a sense global ischemia changes, but the chamber wall etiology may be ischemic, may be toxic, or may be idiopathic. The correct etiology cannot be determined using current methods. In IDCM both left ventricle and right ventricle have decreased levels of Isocitrate + NAD⁺ ⇌ α-ketoglutarate + $CO_2$ + NADH + H⁺  <Eq. 1> mitochondrial enzymes (e.g., cytochromes) and an elevated lactate dehydrogenase level due to increased anaerobic activity secondary to depressed mitochondrial function. Mild mitral regurgitation (MR) is often present in IDCM.

A prognosis of ICDM raises two dilemmas. First, when ICDM is unknown and MR is present it is difficult to distinguish if (a) left ventricular dilation is secondary to severe MR or (b) if left ventricular dilation is secondary to cardiomyopathy which causes MR. In situation (a), treatment would focus on correcting hemodynamics of MR. In situation (b), treatment would focus on correcting the etiology of cardiomyopathy, if possible. To distinguish between the two situations the tissue viability monitor is used to establish the absence or presence of cardiomyopathy. Second, in (a) patients with mild motion abnormalities and/or abnormal Q waves, the etiology may be (a) secondary to myocardial infarction due to coronary artery disease or (b) secondary to myocardial fibrosis due to severe dilated cardiomyopathy. Use of the tissue viability monitor in situation (a) may demonstrate viable but hibernating myocardium in which case angioplasty or surgery for revascularization will be essential to correct the abnormal wall motion. In situation (b), the viability monitor will show decreased amounts of viable tissue in which case surgery or angioplasty will not change the outcome and therefore are not indicated.

B. Evaluation of myocardial toxicity during chemotherapy.

C. Evaluation of types of salvageable myocardium in clinical situations that are present as cardiomyopathy.

D. Detection of myocardial rejection following transplant.

E. Evaluation of myocardial viability following bypass. In many instances there is decreased wall motion following coronary artery bypass. This may be secondary to irreversible reperfusion injury in which case there should be little expectation for recovery. In other cases the etiology of wall motion abnormality is the transient post operative stunning of an otherwise viable myocardium. In this case it is reasonable to expect recovery with improvement in due time with optimization of chemical conditions.

F. Evaluation of myocardial muscle around surgical sites before and after an operative procedure for valve repair, aneurysmectomy and repair.

Cell Mechanisms

Electron Transport Chain and the Role of NADH

The major enzymes or protein components functioning as electron-transfer components in the mitochondrial electron transport system as follows:

1. AND+-linked dehydrogenases

2. Flavin-linked dehydrogenases

3. Iron-sulfur proteins

4. Cytochromes

In the following reaction the function of nicotinamide adenine dinucleotide (AND+)-linked dehydrogenases will be described as a representative of the group.

AND+-linked Dehydrogenases

The initial stage in the mitochondrial electron transport sequence consists of the generation of reducing equivalents in the tricarboxylic acid cycle (TCA), the fatty acid B-oxidation, and various other dehydrogenase reactions. The AND+-linked dehydrogenase reactions of these pathways reduce AND+ to NADH while converting the reduced member of an oxidation-reduction couple to the oxidized form, for example, for the isocitrate dehydrogenase reaction.

Nicotinamide adeninc dinucleotide phosphate (NADP) is involved in similar reactions. In either case, once NADH or NADPH is formed in an oxidation reaction it is released from the primary dehydrogenase and serves as a substrate for the mitochondrial respiratory chain but is used in the reductive biosynthetic reactions and its level is ultimately reflected in NADH levels entering the mitochondrial respiratory chain.

Figures 1A, 1B, 1C, 1D:
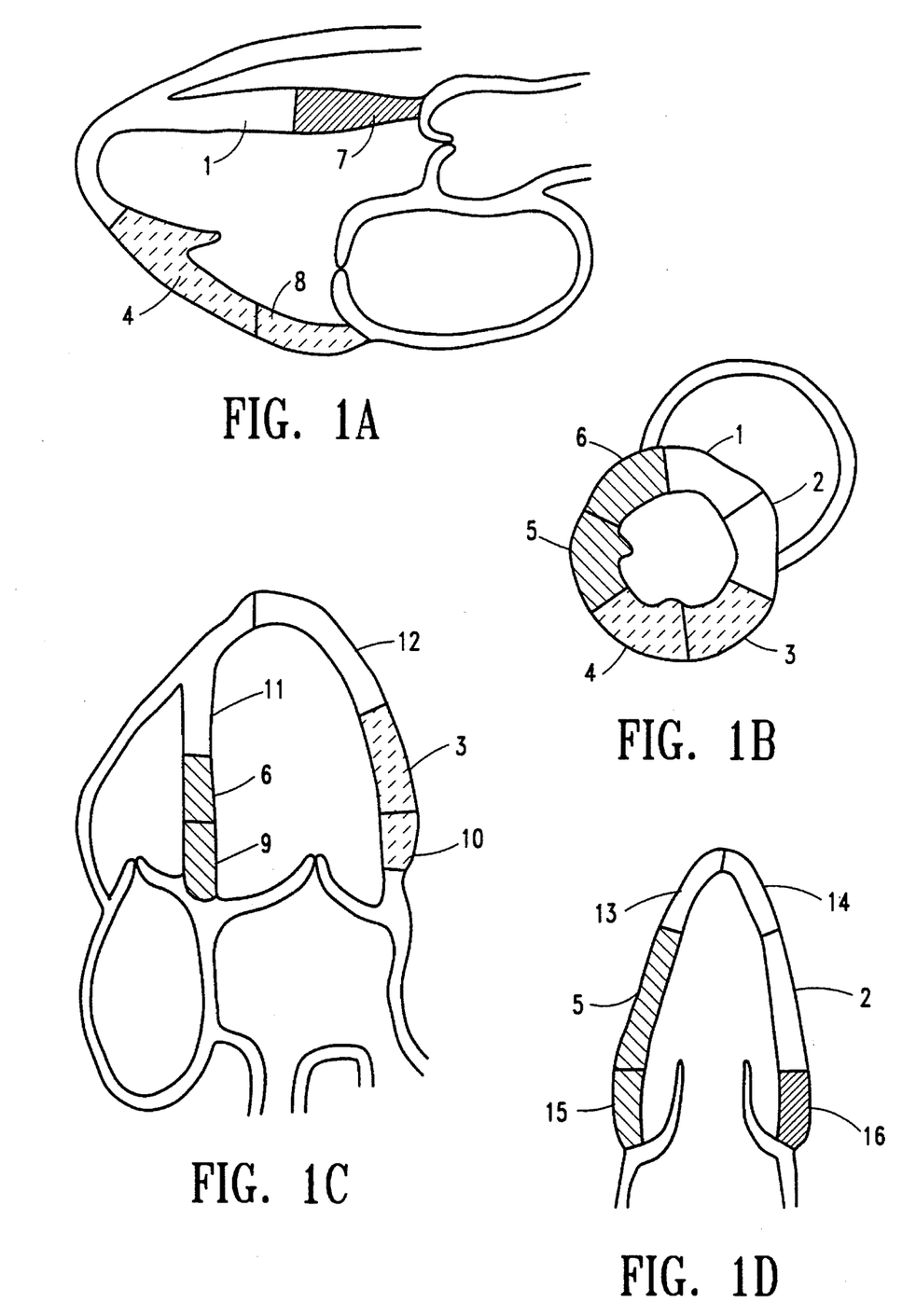
FIGS. 1A, 1B, 1C and 1D illustrate segmentation of the heart for evaluation.
Figure 2:
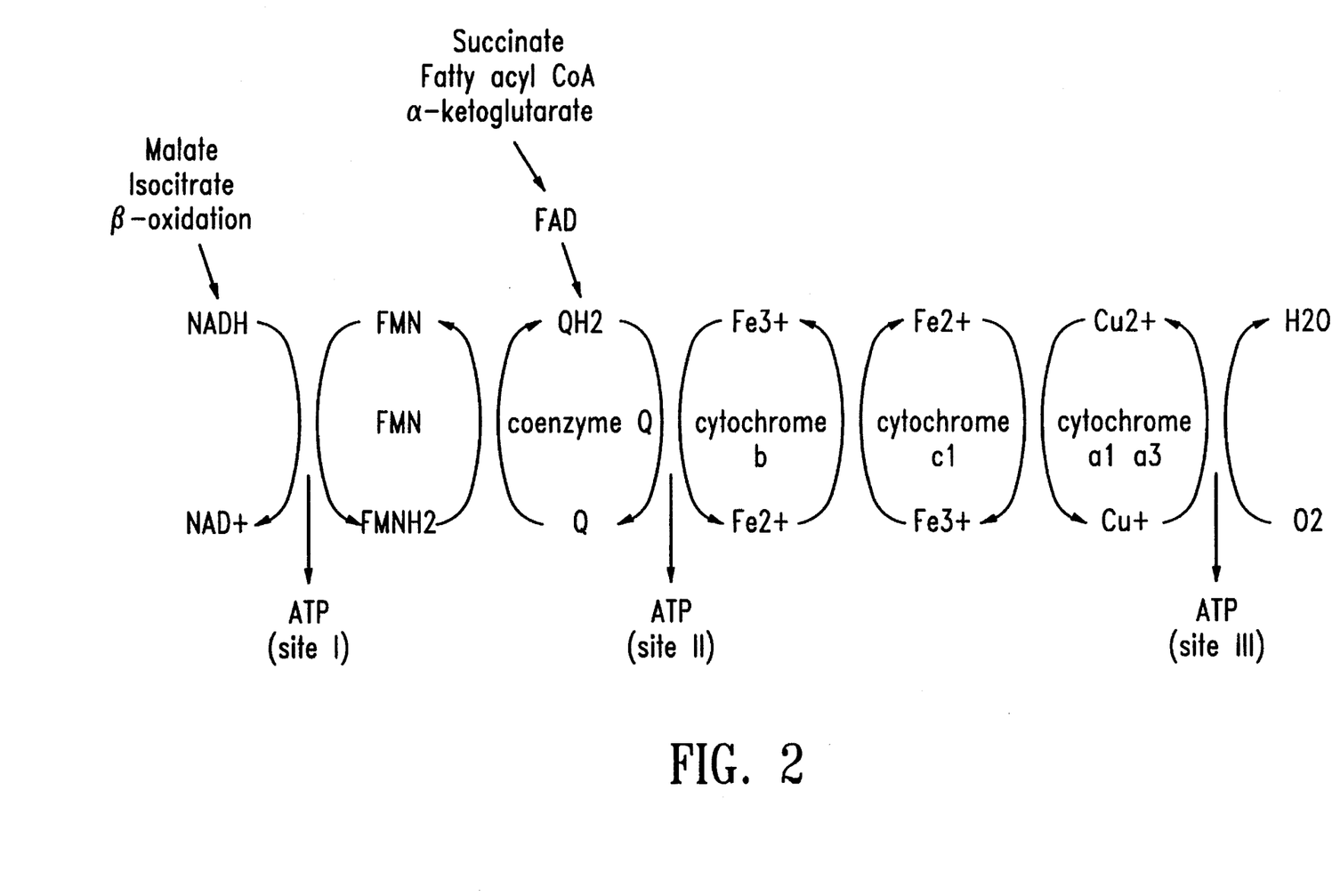
FIG. 2 illustrates the arrangement of the mitochondrial electron transport carriers.

The various electron-transferring proteins and other carriers of the respiratory chain are arranged in a sequential pattern in the inner mitochondrial membrane. Reducing equivalents such as NADH or flavin adeninc dinucleotide (FADH) are extracted from the TCA cycle or fatty acid β-oxidation and indirectly from glycolysis and passed sequentially through the electron transport chain to make molecular oxygen. The arrangement of the mitochondrial electron transport carriers are shown in FIG. 2. In essence, electrons or reducing equivalents are fed into the electron transport chain at the level of NADH or coenzyme Q from the primary AND+-linked or FAD+-linked dehydrogenase reactions and are transported to molecular oxygen through the cytochrome chain. This electron transport system is set up so that the reduced member (XH2) of one redox couple is oxidized (X) by the next component in the system according to the direction of the arrows. For example, in the first step, NADH + FMN ⟶ NAD + FMNH2  <Eq. 2>
(reduced) (oxidized)   (oxidized) (reduced)

It should be noted that the electron transfer reactions from NADH through eoenzyme Q transfer two electrons, whereas the reactions between coenzyme Q and oxygen involving the various cytochromes are one-electron transfer reactions.

During the transfer of the electrons from the NADH / AND+ couple (E0=+0.32) to molecular oxygen (E0=+0.82) there occurs an oxidation-reduction potential decrease of 1.14 V (E0=standard potential energy). These drops in potential occur in three discrete steps (site I, site II, site III in FIG. 2) as reducing equivalents or electrons are passed between the different segments of the chain. There is at least a 0.3 V decrease in the potential between each of the three coupling or phosphorylation sites. A potential drop of 0.3 V is more than sufficient to accommodate the synthesis of a high-energy phosphate bond such as occurs in ATP synthesis. When electrons enter at NADH this results in three ATP molecules generated. When electrons enter at the level of succinate through FADH this results in two ATP molecules generated.

<Eq. 3>

Succinate is formed from the energy-rich succinyl CoA and once formed is oxidized to fumarate in the FAD-linked succinate dehydrogenase reaction of the TCA cycle. It is thought that the non-heme iron of this dehydrogenase undergoes valence changes (oxidation/reduction ($Fe^{2+} \Leftrightarrow Fe^{3+}$)) during the removal of electrons and protons from succinate and the subsequent transfer of these reducing equivalents through FAD to the mitochondrial electron-transfer chain at the coenzyme Q-cytochrome b level.

The succinate precursor succinyl CoA represents a metabolic branch point in that intermediates may enter or exit the TCA cycle at this point. Succinyl CoA may be formed from either a-ketoglutarate in the TCA cycle or from naethyl malonyl CoA, the end product of odd fatty acid chain breakdown. The metabolic fates of succinyl CoA include its conversion to succinate in the TCA cycle or entry into the porphyrin b cosynthesis pathway.

Transport of Succinate into the Mitochondria

Oxidation of succinate through the electron transport chain and its generation in the TCA cycle all occur in the mitochondria. Traffic into this matrix space is brisk but occurs largely either as active transport or as facilitated exchange or through specific proteins highly specialized for this purpose. These proteins are termed porters or translocases, most of which function in an antiport mode, i.e., a substance is assisted in moving across the membrane only in exchange for some rather specific countermoving substance of similar charge, for example ADP for ATP. No external energy supply is required for transport on a translocase (porter). At least one of the pair of transported molecules moving in the antiport (exchange) mode must be moving down a significant concentration gradient. Therefore, the translocases for a pair of substances can be driven in either direction by supplying a higher concentration of the one substance required to enter the compartment or cross the membrane. For example, when succinate is infused into the cellular matrix, it will be present at high concentration and the translocase will be driven by the concentration gradient to transport it into the mitochondria.

Efflux of a major cell constituent along a concentration gradient—whether across the mitochondrial or plasma membrane—can drive the movement of the counter substance against a gradient, thereby doing "work" until the two driving forces have been completed. For operation of the TCA cycle, only the facilitated entry of pyruvate is required. However, other porters are functional to facilitate and replicate intermediates in this cycle (see Eqn. 4, below). Malate entry from the cytosol into the mitochondria provides a source of additional reducing equivalents and makes possible a mechanism for gluconeogenesis. Citrate exit provides a means of exporting acetyl groups. The tricarboxylate carrier transports citrate, isocitrate, aconitate and such dicarboxylates as realate and succinate.

<Eq. 4.>

SUMMARY OF THE INVENTION

Any accurate assessment of tissue viability should be adapted to current methods for treatment to salvage severely but not irreversibly damaged myocardium. Static measurements of vital intracellular high energy compounds has failed to provide the needed information in a significant number of marginal situations.

The method and apparatus of this invention provides a clinically applicable dynamic approach whereby a cell is "provoked" or activated by providing one or more metabolic substrates of the respiratory chain, and directly or indirectly measuring any cellular response to each provocation. In a preferred implementation, the device is carried at the tip of a catheter which can be guided inside the heart during cardiac catheterization. The new probe allows the physician to: 1) position the probe at a tissue of interest, 2) evaluate the initial state of the tissue, 3) diffuse into the tissue basic ingredients needed for cellular respiration and resulting energy production (oxygen, glucose, low energy phosphates); 4) detect the result of this process by measuring substance uptake, oxygen utilization and/or oxidation reduction (redox) stores of the respiratory enzymes; and 5) optionally detect consequent mechanical activity by ultrasound backscatter technique (in conjunction with a second catheter). In general, the physician will also diffuse into the tissue a substrate compound then later a trigger compound and detect the result of this process as well.

Several methods of detection can be used with this invention, including direct chemical measures, indirect chemical measures, e.g. using spectroscopic techniques, or measurement of physiological responses or parameters.

The new method provides an efficient tool applicable to numerous clinical situations where further therapeutic refinement is needed. In addition, the new device provides a research tool to investigate myocardial ischemia more easily and in ways o that are simply not available using current techniques and devices.

Uniqueness of the Viability Monitor

A unique feature of this monitor is the meaning of the measurements obtained. Essentially a tissue viability test provides a material to interrogate (activate) a tissue segment which has been deprived of its vital supply by disease or trauma. The test then determines whether cells in the segment possibly could respond if proper substrate were to be provided, e.g. by restoring some normal function of the tissue. The test functions at two levels. First, a baseline measurement monitors the initial condition of the tissue. Next, a substrate is infused into the tissue. A preferred substrate is a metabolic substrate that will be processed by intact tissue to affect a target intracellular component. Ideally, the substrate will activate an enzyme system which in turn will activate one or more subsequent enzyme systems to provide a cascade or amplification of the original signal when a subsequent metabolic effect is measured. Measuring the tissue at this point, and comparing the measurement to the initial condition, can show if the cellular machinery is intact, which shows whether the cell is viable. A further test can provide even more information. By providing a trigger compound which will further activate the cascade system, a greater response can be measured. For example, if the metabolic system is the respiratory chain, a useful initial substrate is succinate, fumarate or malate. Addition of the substrate increases metabolic activity in the oxidative pathway because of the increased concentration of a starting material. Next, a useful trigger compound is ADP. This increases activity of phosphorylation, which interacts with and amplifies activity in the oxidative pathway and allows a very substantial increase of metabolic activity.

Another test system monitors glucose uptake, then adds glucose as a substrate, again measuring glucose uptake, followed by administration of insulin as a trigger, and again measuring glucose uptake.

A favorable biochemical or consequent physical response by the tissue means that the tissue function may be restored by appropriate medical intervention. In stunned cardiac tissue, revascularization by either percutaneous transluminal angioplasty (PTCA) or coronary artery bypass grafting more than likely will be successful in reversing the compromised function. In essence interrogating the tissue with the viability monitor mimics potential tissue behavior after angioplasty or bypass grafting. Therefore, the tissue viability monitor has several roles:

1. Diagnosis
2. Guide management
3. Predict success of outcome

Reasons for Incorporating New Technology of Viability Monitor Into Standard Clinical Practices and Hospitals With the onset of budgetary constraints in the allied health fields, there is a growing demand by physicians, patients, and administrators to seek more effective methods of evaluation. The tissue viability monitor provides solid, objective information and helps predict the outcome of subsequent major interventions such as thoracic surgery before engaging in such attempts. Many clinical situations arise where there is a controversy about whether a major surgical procedure should be attempted. Is it worth it to take the risk? In the case of a compromised myocardial function, it would be of paramount importance to determine by the use of a viability monitor whether there is myocardium to be salvaged before embarking on major thoracic surgery. Using surgery alone, there is a significant risk of carrying out the surgical procedure only to find that there is no viable myocardium to be salvaged. This kind of information will be instrumental for justification of procedures for all parties involved and will play a role in averting unnecessary major interventions that could be costly with respect to both mortality and finances. The reasons for eagerly accepting and incorporating the tissue viability monitor into standard clinical practice may be summarized as follows:

1. To clarify controversial clinical situations
2. To assess the prognosis for surgical success in high risk situations (to aid cardiologists in surgery recommendations to surgeons)
3. To assess the prognosis for angioplasty (to aid cardiologists in justifying high-risk angioplasty to patients and institutions)
4. To provide objective justifications for the following institutions:
   a) For HMO's, to approve a procedure.
   b) For insurance or government agencies for reimbursement.
   c) To medico-legally support clinical decisions.

DETAILED DESCRIPTION

The device of the present invention is a modified catheter suitable for placement in the tissue of interest. There are a wide variety of steerable catheters well known to eardiologists. Many of these could be modified to provide the device of the present invention. The invention can also be manufactured in the form of a probe rather than a catheter useful, for example, for examining the skin of a patient, but the general design can be understood from the following discussion.

In general, the device provides a sensing apparatus for detecting a selected biochemical or physiological response. In addition, the device provides a means for delivering one or more compounds to the tissue under study. The sensing apparatus may include spectrophotometric apparatus (illumination and detection, e.g. through fiber-optic leads), biochemical monitors (such as a compound-sensitive electrode), temperature monitors, and other devices known in the art.

Figure 3:
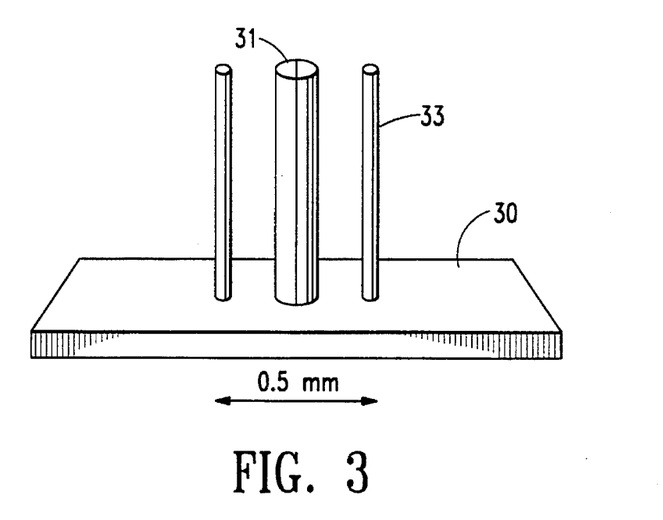
FIG. 3 illustrates a preferred form of the viability probe.

Referring to FIG. 3, center portion 31 of a probe tip 30 can hold a detection device or connections to a detection device. In a preferred form, the probe tip 30 includes two fiber-optic leads, one to carry light to illuminate the area of interest, and the other to collect light from the area for subsequent detection and analysis. The light source and detection equipment are not shown but such apparatus are very well known to one skilled in the art. One useful configuration and apparatus is described in Parsons et al., U.S. Pat. Nos. 5,161,531 and 5,127,409.

The probe tip also includes micropipettes 33, which are connected to a reservoir of material which can be delivered at a specified and controlled rate and time. Apparatus for controlling delivery are well known. A simple application device is a conventional syringe connected to tubing which is connected to micropipette 33. A simple variation of this is an IV AC or other controlled delivery device, such as those used for control of intravenous drip. An electronically controlled metering device is particularly useful.

Figures 4A, 4B:
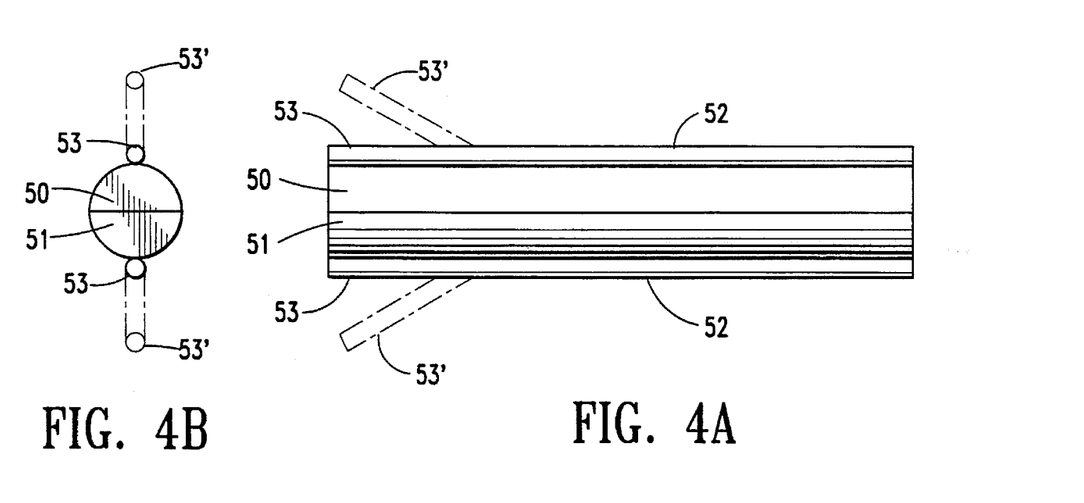
FIGS. 4A, 4B and 4C illustrate another preferred form of the viability probe.
Figure 4C:
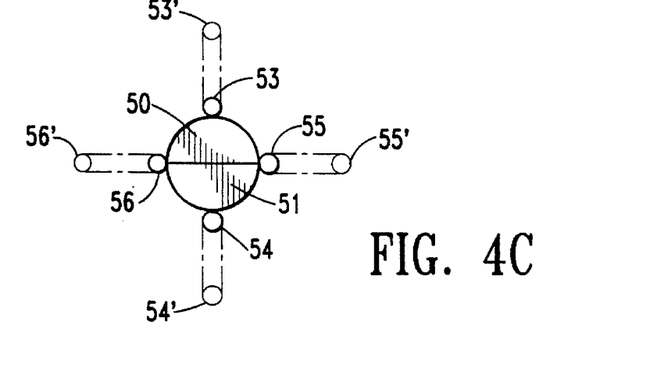

In one preferred embodiment, illustrated in FIGS. 4A, 4B and 4C, the probe is a catheter, somewhat similar to that described in the Parsons references. The central portion of the catheter includes fiber-optic elements 50, 51 to carry illuminating light and detected light. Other lumen elements 52 are included in the catheter and carry fluid to the catheter tip. End portion 53 is connected to 52 to deliver the contained fluid to the tissue of interest. End portion 53 is designed to move to open position 53' to form an umbrella-like structure. In FIG. 4C, several alternate end portions 53, 54, 55 and 56 move to corresponding open positions 53', 54', 55' and 56'. Although the figures illustrate a central fiber-optic portion and outer micropipettes, the actual order of elements can be varied. For example, one useful embodiment include a central core for delivery of fluid and two external fiber optic bundles for transmission of light. Another useful embodiment uses one external fiber optic bundle to deliver illuminating light and two or more external fiber optic bundles for collecting detected light.

The catheter tip is anchored firmly in place by ejecting an "umbrella-like device" with a central portion and peripheral portions. The catheter includes sensing components and fluid transmission components but the specific configuration of each component at the catheter tip can be modified. The important thing is to provide a metabolic substrate or other trigger compound in the presence of tissue which is evaluated using the sensing components.

In one preferred embodiment, the probe tip includes three pods, the center of which contains the sampling probe. This will insure stability of the catheter on the moving myocardial surface. The sampling probe pierces the myocardial wall at a depth equal to one third of the total thickness for that wall. Since the average left ventricle thickness is 6 to 10 mm, one third of this thickness is approximately 3 mm. The cardiologist can control the depth of penetration. The depth will be varied for certain clinical entities as well as in conditions of myocardial hypertrophy.

Once the probe is positioned on the tissue of interest, a baseline measurement is taken. A substrate compound is infused into the tissue as additional measurements are taken. In many instances, it is advantageous to infuse a second substance, a trigger compound, while continuing to take measurements.

One preferred implementation uses a variation of the Parsons et al. device to monitor activity of cytochrome a, a3. The probe illustrated in FIG. 4A is positioned in an area of interest and spectrophotometric measurements are taken. In general, the measurements will be taken continuously but it may be sufficient to take measurements at selected times. A substrate is infused, preferably succinate, and additional measurements or taken. If there is any response at all, the tissue can be considered to have some potential viability. After some time, generally one to ten minutes, a second, trigger compound can be added. In a preferred implementation, the trigger compound is ADP. Additional measurements are taken, again looking for an increase in signal. It is relatively easy to observe a 10% change in a spectrophotometric signal, and for many tissue samples the response upon administration of substrate, sometimes after trigger, is on the order of a 100% increase in signal.

Positioning of the Tissue Viability Monitor Catheter Tip for Sampling

The tissue viability monitor is used to assess viability of "segments" of the myocardial walls. The myocardial walls, right ventricle, interventricular septum, and left ventricle are divided into sixteen segments, each section corresponding to a region supplied by a significant coronary artery. These segments have been defined based on the images obtained by echocardiography. FIG. 1A–D demonstrate preferred standard views used in echocardiography and the division of the myocardial walls. Each wall segment is named, indexed in the figures with a corresponding number (1–16). The name essentially describes the type of wall (septum or wall "of ventricle") and its location by one or two vectors, e.g., inferior, inferior lateral, or apical inferior.

Furthermore, each segment can be pattern-coded according to the index. Each pattern identifies the blood supply to that segment from a specific coronary artery. Segments of the same pattern receive the blood supply from the same coronary artery. For example, segments 1, 2, and 11–14 receive the blood supply from the left anterior descending (LAD) coronary artery.

|    | Wall Motion Segment | Coronary Artery |
|----|---------------------|-----------------|
| 1  | Mid Ant Sept        | LAD             |
| 2  | Mid Ant             | LAD             |
| 3  | Ant Lat             | LCX             |
| 4  | Inf Lat             | LCX             |
| 5  | Inf                 | RCA (FDA)       |
| 6  | Inf Sept            | RCA (FDA)       |
| 7  | Basal Ant Sept      | LAD (Prox)      |
| 8  | Basal Post          | LCX             |
| 9  | Basal Sept          | RCA (FDA)       |
| 10 | Basal Lat           | LCX             |
| 11 | Apical Sept         | LAD             |
| 12 | Apical Lat          | LAD             |
| 13 | Apical Inf          | LAD             |
| 14 | Apical Ant          | LAD             |
| 15 | Basal Inf           | RCA (FDA)       |
| 16 | Basal Ant           | LAD (Prox)      |

LAD—Untitled; LAD (Prox)—back slant (lines descending right to left); LCX—speckled; RCA (FDA)—forward slant (lines descending left to right).

Each segment is several centimeters long. An experienced cardiologist can easily position a catheter tip within a region of this size. In contrast, during electrophysiology-mapping the electrode catheter has to identify and be placed in alignment with electrical accessory pathways which are millimeters or fractions of a millimeter wide, requiring time-consuming positioning maneuvers and a high degree of precision. This problem is not pertinent to the tissue viability monitor.

For the tissue viability monitor, the tip of the sensing catheter preferably is positioned at or near the center of one or more of these defined wall segments. Such a catheter therefore will have maneuverability characteristics similar to standard catheters presently in use where gross positioning is easily achieved. Positioning of the catheter on each wall segment is guided and verified by fluoroscopy comparable to the standard technology used during the positioning of catheters for catheterization of tiny orifices of the coronary arteries.

Each segment is sampled once or twice from the central area of each segment. Normally three to four segments in the vicinity of the myocardial wall of concern is evaluated. The results can be scored in a variety of ways. For example, a simple gross quantitative value can be used to compare observations. In a preferred embodiment, a scale of 0–5 is used, 0) unable to score, 1) normal, 2) hypokinetic, 3) axikinetic, 4) dyskinetic, and 5) aneurysmal. One skilled in the art can devise alterative scoring systems.

Risk of Arrhythmia

There is a recognized risk for the occurrence of limited, transient arrhythmia during an intracardiac catheter placement, e.g., cardiac catheters, electrophysiology pacing wires, or biopsy devices. These arrhythmias occur, usually transiently, as the catheter touches specific sensitive, excitable focus areas in the myocardial wall. Usually the arrhythmia self-terminates once the catheter is repositioned away from the excitable focus.

In rare cases an arrhythmia does not self-terminate. A good cardiac catheterization laboratory and known procedures are designed to handle such arrhythmia by either activating temporary pacing wires, usually pre-positioned in the heart prior to attempting catheterization, or by intravenously infusing appropriate pharmacological agents. In either case, cardiac catheterization is performed daily and control of transient arrhythmias is well handled in the cath-lab or, rarely, in the intensive care unit, the only locations where catheterization should be attempted.

The tissue viability monitor catheter and procedure are not significantly different than standard catheters in their potential to induce limited transient arrhythmias during positioning.

Length of Time to Do Measurements

Response and stabilization of the tissue viability monitor of the activating metabolic signal should be achieved within minutes. Positioning of the catheter probe on a particular myocardial wall segment should also be achieved within minutes, perhaps similar to the time required to position a myocardial biopsy catheter on a selected portion of the myocardium. In any such placement, certain locations in the myocardial wall may be less easily accessible than others. Experienced physicians can position the catheter more quickly after repeated or frequent use. In general, the total time for the procedure is less than thirty minutes, significantly shorter than the time required to do percutaneous transluminal angioplasty (PTCA).

Metabolic Considerations

Oxygen consumption may be measured by the tissue viability monitor; however, as discussed above, because of the dynamic nature of the measurement, the oxygen consumption measurement by this technology may not be a valid indicator of viability.

One useful substrate for practicing the invention is succinate. Succinate is available in high purity (chromatographic grade) from Sigma Chemical Co. Standard procedures are available to prepare the material for intravenous administration. The amount to be administered is very low in terms of whole body exposure, while local concentrations are generally close to normal physiological ranges.

Glucose uptake is a property of viable tissue. The glucose uptake process obtains its energy from the chemical gradient present across the cell membrane. This chemical gradient is established by active pumping of sodium to the outside and potassium to the inside of the wall by the ATP-dependent sodium-potassium pump. This gradient has a potential of −90 mV (millivolts). To establish and maintain this gradient, the cell membrane has to be intact and ATP-dependent pumps must be viable. Cell viability requires maintenance of the potential across the cell membrane. Dead cells, irreversibly damaged cells and non-salvageable cells do not have this capacity and therefore cannot transport glucose across the cell membrane in an active fashion, particularly when a stimulus such as insulin introduced.

Similarly the electron transport chain within the mitochondria requires for its proper functioning the presence of a strong chemical/ionic gradient across the mitochondrial membrane (the chemiosmotic hypothesis). Failure of this gradient, or failure of the cellular gradient which in turn affects the mitochondrial gradient, will compromise function of the electron transport chain.

Electron transport chain activity in isolated mitochondria is different than corresponding activity in intact cells and tissue. This activity, then, can be used as an indicator of whether or not the cells are intact and capable of functioning. In conclusion, therefore, many, if not all, ionic gradient-dependent dynamic measurements (e.g., electron transport, cytochrome activity, or glucose uptake) are significantly affected by cell viability.

A cell may be compromised to varying degrees depending on the trauma that initiated cell injury and the time since the trauma. Since one or more intermediate states of so-called "reversible damage" may exist, the tissue viability monitor can be used to quantify grades of viability.

The tissue viability monitor of this invention incorporates backscatter technology. Therefore, development of the probe will contribute to the development of backscatter technology. Furthermore, any advances in backscatter technology over the next few years can be incorporated within the viability probe. However, it should be clear that information obtained by backscatter technology either transthoracic or on a catheter does not represent an objective measurement of ischemia or viability. In contrast, measurements of metabolic alterations represented by glucose transport or the electron transport chain provides solid objective information regarding viability.

The main users of the tissue viability monitor initially will be cardiologists in the cardiac catheterization lab and surgeons intraoperatively.

The general teachings of this invention can be utilized to monitor the viability of other organs and the device and method can be used by other sub-specialists, including gastroenterologists and interventional radiologists. Organs and areas of particular interest include large and small intestines, kidney, liver, brain, and extremities. Intestinal infarct can be life threatening. After transplant of any organ, it would be helpful to use the new device to examine tissue in the transplanted organ and possibly in other host tissues as well.

Liver or kidney can become fibrotic, leading to loss of function in the organ. Using the new invention, a catheter can be directed though the renal artery to probe selected portions of the renal cortex. A probe also might be inserted through an incision in the abdomen to examine either the liver or kidney. The new invention may be particularly helpful in examining these organs. At present, about the only way to effectively probe the liver and kidney is during autopsy after the patient has died. The new invention could be used earlier in order to ascertain whether any medical intervention might have a reasonable chance of success and keep the patient alive.

The new invention may be useful in examining muscle and other tissue in various body parts. One significant application is in examining skin after a grafting procedure. The probe can be applied eternally. Another significant application is in examining gangrenous or necrotic tissue, such as muscle or connective tissue, in extremities. These conditions often arise in severe or late stage diabetes, atherosclerosis or after a clot, burn or trauma affecting the region of interest.

A general description of the device and method of the present invention as well as preferred embodiments of the present invention have been set forth above. One skilled in the art will recognize and be able to practice many changes in many aspects of the device and method described above, including variations which fall within the teachings of the invention. The spirit and scope of the invention should be limited only as set forth in the claims which follow.

We claim:

1. A method of determining the viability of tissue comprising the steps of measuring a characteristic of an intracellular component, infusing a substrate compound and measuring the characteristic of the intracellular component after infusion of the substrate compound.

2. The method of claim 1 where the measuring steps comprise measuring a characteristic of an intracellular component of myocardial tissue.

3. The method of claim 1 where the measuring steps comprise measuring a characteristic of an intracellular component of contractile tissue which is stunned or hibernating.

4. The method of claim 1 where the measuring steps comprise measuring a characteristic of an intracellular component of contractile tissue with reduced or no contractility.

5. The method of claim 1 where the steps of measuring the characteristic of the intracellular component comprise measuring the concentration of said intracellular component.

6. The method of claim 1 where the steps of measuring the characteristic of the intracellular component comprise measuring the activity of said intracellular component.

7. The method of claim 1 where the steps of measuring the characteristic of the intracellular component comprise measuring oxidative metabolism involving the intracellular component.

8. The method of claim 1 where the steps of measuring the characteristic comprise performing spectrophotometric evaluation of the intracellular component.

9. The method of claim 8 where the steps of performing spectrophotometric evaluation of the intracellular component comprise irradiating the tissue with a visible light wavelength radiation and detecting the radiation.

10. The method of claim 8 where the steps of performing spectrophotometric evaluation of the intracellular component comprise irradiating the tissue with a near infrared light wavelength radiation and detecting the radiation.

11. The method of claim 10 where the steps of performing spectrophotometric evaluation of said intracellular component comprise irradiating the tissue with a plurality of near infrared light wavelengths radiation and detecting the radiation.

12. The method of claim 1 where the steps of measuring the characteristic of the intracellular component comprise measuring an enzyme.

13. The method of claim 1 where the steps of measuring the characteristic of the intracellular component comprise measuring cytochrome.

14. The method of claim 1 where the step of infusing a substrate compound comprises infusing a metabolic substrate.

15. The method of claim 1 where the step of infusing a substrate compound comprises infusing a metabolic substrate for an enzyme in the oxidative metabolism redox chain.

16. The method of claim 1 where the step of infusing a substrate compound comprises infusing a compound selected from the group consisting of malate, fumarate and succinate.

17. The method of claim 1 where the step of infusing a substrate compound comprises infusing a compound known to modify the action of the intracellular component.

18. The method of claim 1 further comprising the step of a trigger compound after infusion of the substrate compound.

19. The method of claim 18 where the step of infusing a substrate compound comprises infusing glucose and where the step of infusing a trigger compound comprises infusing insulin.

20. The method of claim 18 where the step of infusing a trigger compound comprises infusing adenosine diphosphate.

* * * * *